(12) United States Patent  
Williams

(10) Patent No.: US 7,951,296 B2  
(45) Date of Patent: May 31, 2011

(54) APPARATUS AND METHOD FOR AGRICULTURAL ANIMAL WASTEWATER TREATMENT

(75) Inventor: Scott Reid Williams, Beulaville, NC (US)

(73) Assignee: Scott R. Williams, Beulaville, NC (US)

( * ) Notice: Subject to any disclaimer, the term of this patent is extended or adjusted under 35 U.S.C. 154(b) by 227 days.

(21) Appl. No.: 12/420,013

(22) Filed: Apr. 7, 2009

(65) Prior Publication Data

US 2009/0250393 A1    Oct. 8, 2009

Related U.S. Application Data

(60) Provisional application No. 61/043,117, filed on Apr. 7, 2008.

(51) Int. Cl.
*C02F 3/28* (2006.01)
*C02F 11/10* (2006.01)
*C02F 3/32* (2006.01)

(52) U.S. Cl. ... 210/602; 210/603; 210/631; 210/170.08; 71/10

(58) Field of Classification Search ............ 210/602, 210/603, 610, 631, 170.01, 170.08, 252, 210/259; 71/10
See application file for complete search history.

(56) References Cited

U.S. PATENT DOCUMENTS

| | | | | |
|---|---|---|---|---|
| 4,169,050 A | * | 9/1979 | Serfling et al. | 210/602 |
| 4,424,064 A | * | 1/1984 | Klass et al. | 48/197 A |
| 6,106,717 A | * | 8/2000 | Hasegawa et al. | 210/607 |
| 6,129,844 A | * | 10/2000 | Dobelmann | 210/602 |
| 6,692,641 B2 | * | 2/2004 | DeBusk et al. | 210/602 |
| 2002/0117443 A1 | * | 8/2002 | Bailey et al. | 210/602 |
| 2009/0321349 A1 | * | 12/2009 | Offerman et al. | 210/603 |

* cited by examiner

*Primary Examiner* — Fred Prince

(57) ABSTRACT

One embodiment of an apparatus and method for treating agricultural animal wastewater that costs less to build, is easy to operate, and requires little energy input. The method employs natural systems for wastewater treatment; an initial anaerobic digestion treatment followed by batch floating aquatic plant treatment. The batch floating aquatic plant treatment of effluent and subsequent batch discharge provides increased control of the treatment process. Opportunistic collection and use of biogas and floating aquatic biomass results in additional benefits. The apparatus reduces the cost and land area required for the system by subdividing a lagoon into an anaerobic digestion treatment zone below the apparatus and a floating aquatic plant treatment zone above the apparatus. In addition, the apparatus is disposed in the lagoon in such a way that it facilitates the collection of biogas evolving from anaerobic digestion treatment beneath the apparatus by diverting it to areas to be collected.

29 Claims, 8 Drawing Sheets

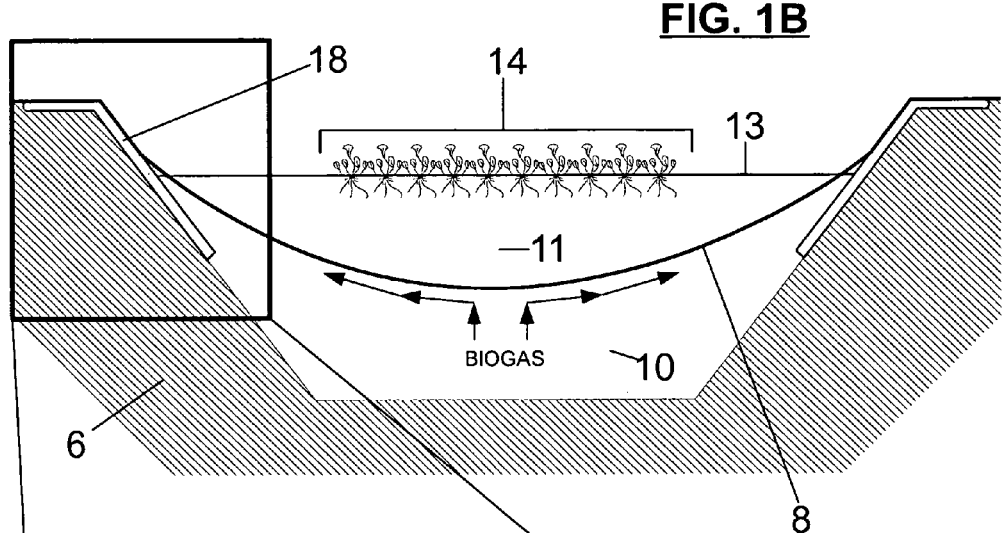
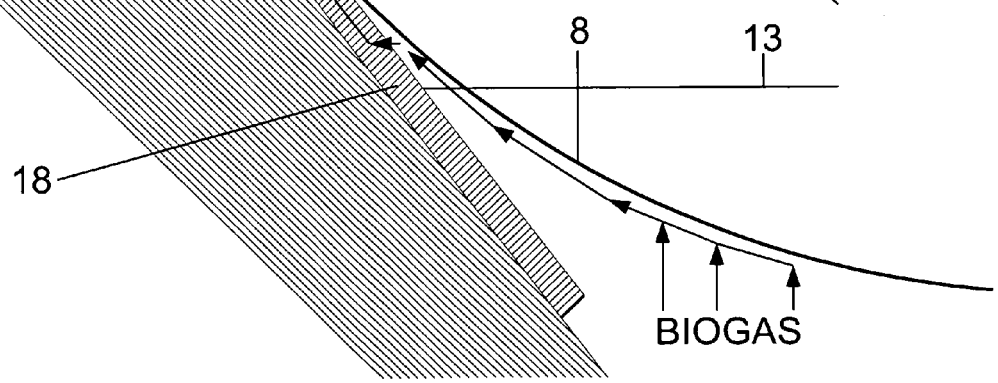

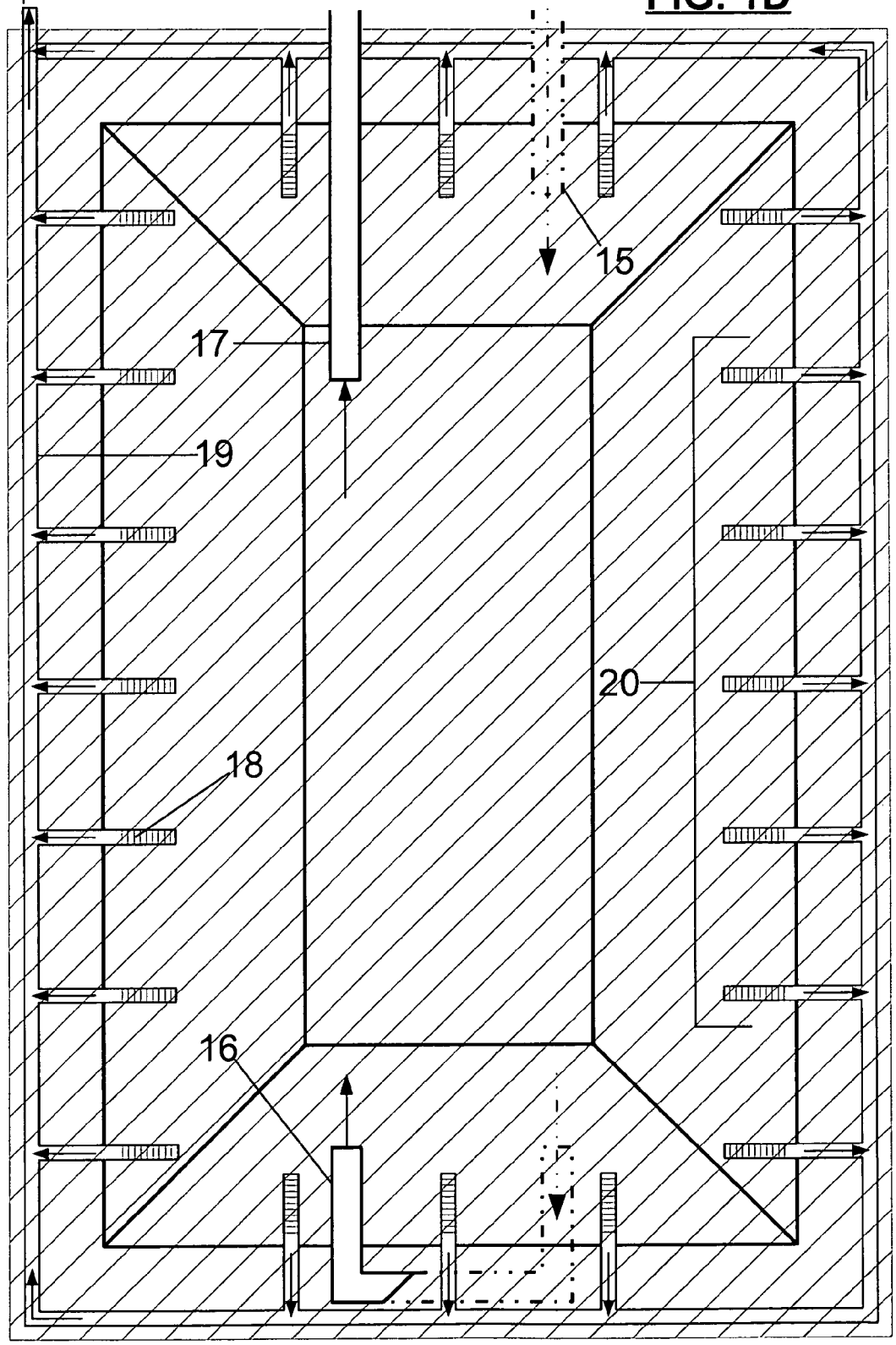

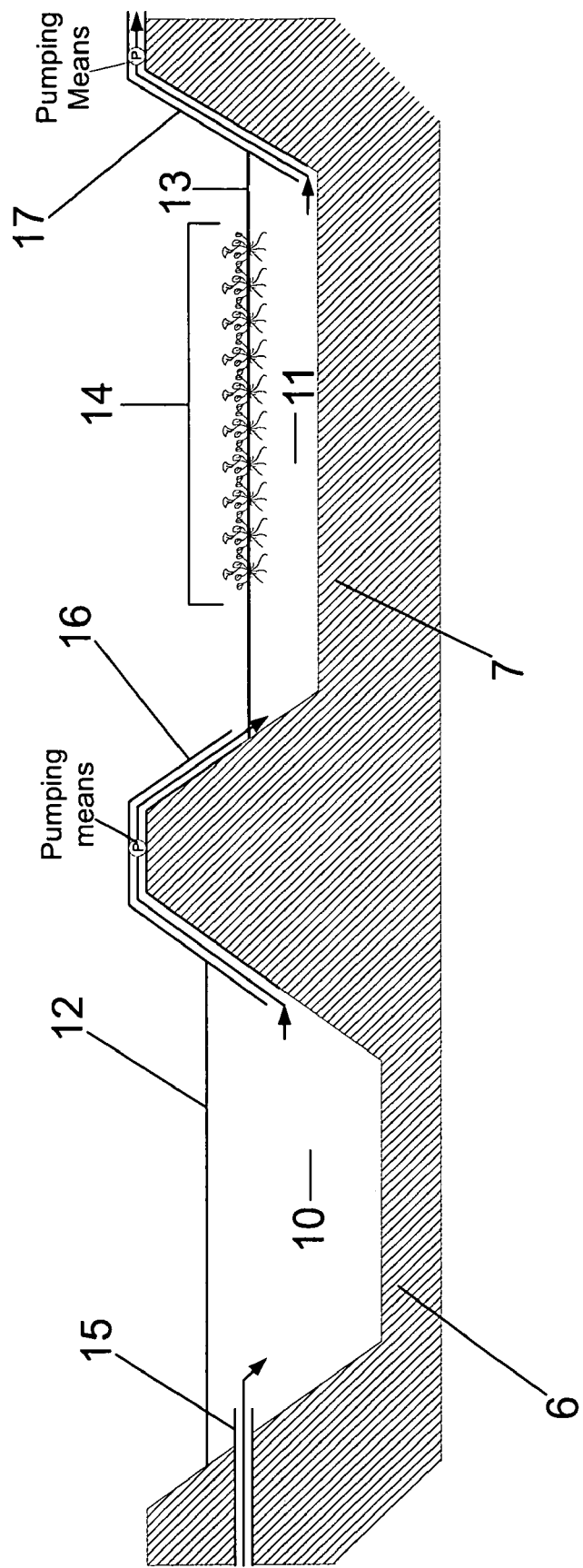

APPARATUS AND METHOD FOR AGRICULTURAL ANIMAL WASTEWATER TREATMENT

CROSS-REFERENCED TO RELATED APPLICATIONS

This application claims the benefit of provisional patent application No. 61/043,117 filed Apr. 7, 2008 by the present inventor.

FEDERALLY SPONSORED RESEARCH

Not Applicable

SEQUENCE LISTING OR PROGRAM

Not Applicable

BACKGROUND OF THE INVENTION

1. Field

This application generally relates to an apparatus and method for wastewater treatment and more specifically to an apparatus and method incorporating natural systems for treatment and management of agricultural animal wastewater.

2. Prior Art

Agricultural animal waste disposal is a major problem. Over the past several decades, increased demand for meat and dairy products has facilitated the rapid growth of the commercial livestock industry. The increased demand and subsequent growth of the industry has led to the utilization of more centralized higher capacity farming operations. These farming operations are sometimes referred to as concentrated animal feeding operations (CAFO's). While these CAFO's may be more productive and cost efficient, they come with the down side of manure management issues. As the commercial livestock industries use of CAFO's has increased, so has environmental concerns over the impact their manure waste has on water and air quality.

Environmental concerns over manure waste from CAFO's are especially pronounced for CAFO's that produce liquid manure waste that is treated and managed using lagoon-spray field systems. Lagoon-spray field systems are systems that generally treat liquid manure waste in large anaerobic lagoons and then intermittently dispose of it through land applications. This system was developed in the early and mid twentieth century prior to the current trend in high concentrated livestock operations. As the livestock industry has expanded, treatment of liquid manure waste using lagoon-spray field systems has come under increased public and governmental scrutiny due to environmental concerns over leaks, spills, odors, and ammonia emissions from the anaerobic lagoons as well as the high nutrient content of the lagoon effluent that is applied to spray fields. Lagoon effluent often contains high levels of biochemical oxygen demand (BOD), Nitrogen (N), and Phosphorus (P) that cannot be decreased to acceptable levels by anaerobic treatment alone. In recent years, States and Federal agencies have promulgated strict rules and regulations governing lagoon-spray field systems in agricultural operations. In some cases, moratoriums on the use or permitting of new lagoon-spray field systems have been enacted.

The swine farming industry in North Carolina is a great example of a commercial livestock industry that has migrated to the use of CAFO's over the past several decades and still primarily uses lagoon-spray field systems to treat and manage liquid manure waste. In 1998 the State of North Carolina enacted a moratorium that prevented the construction and permitting of new lagoon-spray field systems until an environmentally superior waste management technology or process could be developed. In 2000 and 2002, the Attorney General of North Carolina entered into agreements with private companies to promote the identification and development of environmentally superior waste management technologies for use on North Carolina swine farms owned by the companies. This agreement is commonly referred to as the "Smithfield Agreement". The Smithfield Agreement defines an environmentally superior technology (EST) as any technology, or combination of technologies that:

1. is permittable by the appropriate governmental authority,
2. is determined to be technically, operationally and economically feasible for an identified category or categories of farms as described in the agreements, and
3. meets the following performance standards:
   a) Eliminates the discharge of animal waste to surface waters and groundwater through direct discharge, seepage or runoff,
   b) Substantially eliminates atmospheric emissions of ammonia,
   c) Substantially eliminates the emission of odor that is detectable beyond the boundaries of the parcel or tract of land on which the swine farm is located,
   d) Substantially eliminates the release of disease-transmitting vectors and airborne pathogens, and
   e) Substantially eliminates nutrient and heavy metal contamination of soil and groundwater.

These basic requirements for an EST are also codified in North Carolina Administrative Code 15A NCAC 02T.1307—Swine Waste Management System Performance Standards and by proxy in 15A NCAC 02T.1308—Evaluation and Approval of Swine Waste Management Systems. Several of the EST candidates evaluated under the Smithfield Agreement are listed below:

1. Solids Separation/Nitrification-Denitrification/Soluble Phosphorus Removal/Solids Processing System (U.S. Pat. No. 6,893,567).
2. ORBIT—High Solids Anaerobic Digester.
3. Ambient Temperature Anaerobic Digester and Greenhouse for Swine Waste Treatment and Bioresource Recovery.
4. Solids Separation-Reciprocating Wetland.
5. Ekokan Upflow Biofilter.
6. Belt Manure Removal and Gasification System to Convert Dry Manure Thermally to a Combustible Gas Stream for Liquid Fuel Recovery.
7. Solids Separation/Combustion for Energy and Ash Recovery.
8. Solids Separation/Constructed Wetlands System.
9. Sequencing Batch Reactor.
10. Manure Solids Conversion to Insect Biomass—Black Soldier Fly Project.
11. ISSUES—Innovative Sustainable Systems Utilizing Economical Solutions.

Although considerable time, money, and effort has been put towards developing an EST in North Carolina, an EST candidate has yet to be developed or identified that meets the definition of an EST, nor has a candidate reached permittable status. As a result, in 2007 with the passing of Senate Bill 1465, the State of North Carolina converted what had been a temporary 10 year moratorium on lagoon-spray field systems into a permanent moratorium. This has permanently curtailed the growth of the industry in North Carolina until a solution to the problem is found.

While the lagoon-spray field system problem and well defined requirements for a solution described here are specific to North Carolina, the problem and its solution are applicable far beyond the boarders of North Carolina. The situation in North Carolina is simply a microcosm of the broader manure management problem the commercial livestock industry is facing across the United States. In addition to the EST candidates evaluated under the Smithfield Agreement listed above, the following are additional prior art examples of efforts to improve agricultural animal waste treatment with similar disadvantages; U.S. Pat. No. 4,432,869 (Groeneweg et al.), U.S. Pat. No. 5,078,882 (Northrop), U.S. Pat. No. 5,135,659 (Wartanessian), U.S. Pat. No. 5,137,625 (Wolverton), U.S. Pat. No. 5,200,082 (Olsen et al.), U.S. Pat. No. 5,545,560 (Chang), U.S. Pat. No. 5,863,434 (Masse et al.), U.S. Pat. No. 5,885,461 (Tetrault et al.), U.S. Pat. No. 6,083,386 (Lloyd), U.S. Pat. No. 6,113,788 (Molof et al.), U.S. Pat. No. 6,139,743 (Park et al.), U.S. Pat. No. 6,190,566 (Kolber), U.S. Pat. No. 6,284,054 (Galvin), U.S. Pat. No. 7,001,512 (Newsome), U.S. Pat. No. 7,279,104 (Keeton, Jr.), U.S. Pat. No. 7,422,680 (Sheets, Sr.), U.S. Pat. No. 7,481,935 (Olivier).

One of the main problems with many of the prior art examples listed above and the industries approach to the problem in general is that the focus has tended to be on technologies and processes that are more appropriate for large scale waste treatment operations. e.g. solids separation, aeration, heating etc. While CAFO's are by name "concentrated", the volume of wastewater they produce is rather decentralized as compared to advanced wastewater treatment facilities that take advantage of economies of scale. Waste treatment technologies that can meet the "technically feasible" requirements of an EST have existed for years but are too expensive and complicated to construct and operate at the farm level. They are expensive to build, are too complicated operate without significant oversight, and have high energy requirements. The key to solving the problem lies in finding an adequate treatment process that is also "economically and operationally feasible" for the farmer and commercial livestock industry. This thought is echoed by the following statement on the North Carolina State University College of Agriculture and Life Sciences' Smithfield Agreement website: "The swine industry is an important part of North Carolina's economy. The alternative waste management technologies being evaluated are designed not only to treat waste in a manner that protects the environment but also to treat waste in an economically feasible manner that allows the swine industry to survive" [6].

Another problem with many of the prior art examples listed above, and the industries approach to the problem in general is that they have tended to focus on year round treatment of waste. Treatment systems utilizing year round treatment and frequent or continuous discharge are more difficult to permit as the regulatory community less likely to permit a treatment system where there is little opportunity for management and oversight of the discharges. Year round treatment is especially problematic for treatment systems that employ predominantly natural systems for waste treatment (e.g. wetlands) due to the fact that the winter temperatures experienced for most of the United States have a negative effect on their operation. While all waste treatment methods rely on natural responses such as gravity for sedimentation or natural components such as biological organisms, a natural system for waste treatment depends primarily on its natural components to achieve the intended purpose. A natural system might typically include pumps and piping for waste conveyance but would not depend on external energy sources exclusively to maintain the major treatment responses [5]. As such, a natural system (or systems) for waste treatment has an advantage in that it would cost less to build, is easy to operate, and requires less energy. However, these natural systems have not proved to be an adequate solution to the problem because of reduced effectiveness during the colder winter months.

Specifically, many of the prior art examples listed above have one or more of the following problems:

1. they employ a considerable amount of new infrastructure or equipment with moving parts which results in the upfront capital costs being too high to be economically feasible,
2. they have high operational energy requirements which prevents them from being operationally or economically feasible,
3. they are often just too complicated for the average farmer to operate without significant oversight which prevents them from being operationally feasible,
4. natural systems that could be operationally and economically superior have reduced effectiveness during the colder months of the year which prevents them from being technically feasible.

While various systems have been developed for treating agricultural animal wastewater, including the EST candidates and prior art listed above, there still remains a need in the art for a technically, operationally, and economically feasible agricultural animal wastewater treatment system that costs less to build, is easier to understand and operate, and requires little energy input. A method based primarily on natural systems for agricultural animal wastewater treatment has the best chance for succeeding as these systems require less equipment with moving parts, have low operational energy requirements, and are simple for farmers to understand and use.

SUMMARY

For the purpose of summarizing the invention and this specification, one embodiment of the apparatus and method is a technically, operationally, and economically feasible agricultural animal wastewater treatment system that costs less to build, is easier to understand and operate, and requires little energy input.

The method predominantly employs natural systems for wastewater treatment; an initial anaerobic digestion treatment in one zone followed by batch floating aquatic plant treatment in a second zone. Temporary storage capacity in one or both treatment zones allows for batch floating aquatic plant treatment in the second zone and subsequently batch discharges. The batch floating aquatic plant treatment of effluent following anaerobic digestion treatment and the subsequent batch discharge provides increased control of the treatment process. For example, the batch of anaerobic digestion treatment effluent can receive floating aquatic plant treatment until treatment goals are met which allow for discharge or reuse. In addition, for locations where climatic conditions are not ideal year round, this increased process control allows for batch floating aquatic plant treatment to only take place during the growing season of the floating aquatic plants utilized for treatment.

The apparatus reduces the land area and upfront construction cost required for the system by subdividing an existing or newly constructed anaerobic lagoon to create an anaerobic digestion treatment zone below a sheet of material and a floating aquatic plant treatment zone above the sheet of material. In addition to reducing the land area required for treatment, the sheet of material is disposed in the lagoon such that it facilitates the collection of biogas evolving from anaerobic digestion treatment beneath it by diverting biogas to areas to be collected.

Both of the natural systems for wastewater treatment employed by the method described here produce useful byproducts. Anaerobic digestion produces biogas and floating aquatic plant treatment produces floating aquatic plant biomass. The opportunistic collection and use of biogas and floating aquatic plant biomass result in additional benefits. In this embodiment, the floating aquatic plant biomass is placed into the anaerobic digestion treatment zone where it is digested to produce additional biogas. The additional biogas produced results in more cost effective biogas capture and shortens the payback period for the biogas infrastructure. Digesting the floating aquatic plant biomass on site in the anaerobic digestion treatment zone also eliminates transportation costs, one of the problems with utilizing floating aquatic plant biomass for a useful purpose.

Other advantages of one or more aspects of the apparatus and method are that it:
1. Eliminates the discharge of animal waste to surface waters and groundwater,
2. Substantially eliminates atmospheric emissions of ammonia,
3. Substantially eliminates the emission of odor,
4. Substantially eliminates the release of disease-transmitting vectors and airborne pathogens, and
5. Substantially eliminates nutrient and heavy metal contamination of soil and groundwater.

DRAWINGS

Figures

FIG. 1A is a cross section view of an anaerobic lagoon and one embodiment of the apparatus. The anaerobic lagoon structure depicted in FIG. 1A equally represents an existing or newly constructed anaerobic lagoon. Please note that due to the size and shape of anaerobic lagoons, the vertical dimension of FIG. 1A is exaggerated.

FIG. 1B is a cross section view of an anaerobic lagoon and one embodiment of the apparatus that illustrates how the sheet of material diverts biogas evolving from anaerobic digestion treatment to a be collected by a biogas collection means. The anaerobic lagoon structure depicted in FIG. 1B equally represents an existing or newly constructed anaerobic lagoon. Please note that due to the size and shape of anaerobic lagoons, the vertical dimension of FIG. 1B is exaggerated.

FIG. 1C is a close up cross section view of one embodiment of a biogas collection means. FIG. 1C illustrates a perforated pipe that provides a preferential pathway for biogas to escape from below the sheet of material, as well as non-perforated piping to convey captured biogas.

FIG. 1D is a top view of an anaerobic lagoon with one embodiment of a biogas collection means disposed in it. FIG. 1D illustrates a plurality of perforated pipes that provide preferential pathways for biogas to escape from beneath the apparatus' sheet of material, as well as non-perforated piping to convey captured biogas. In FIG. D the sheet of material portion of the apparatus is shown as a transparent hatched area.

FIG. 3 is a cross section view of a two lagoon embodiment illustrating an alternate way the method could be implemented. Please note that due to the size and shape of lagoons, the vertical dimension of FIG. 3 is exaggerated.

Figure 1A:
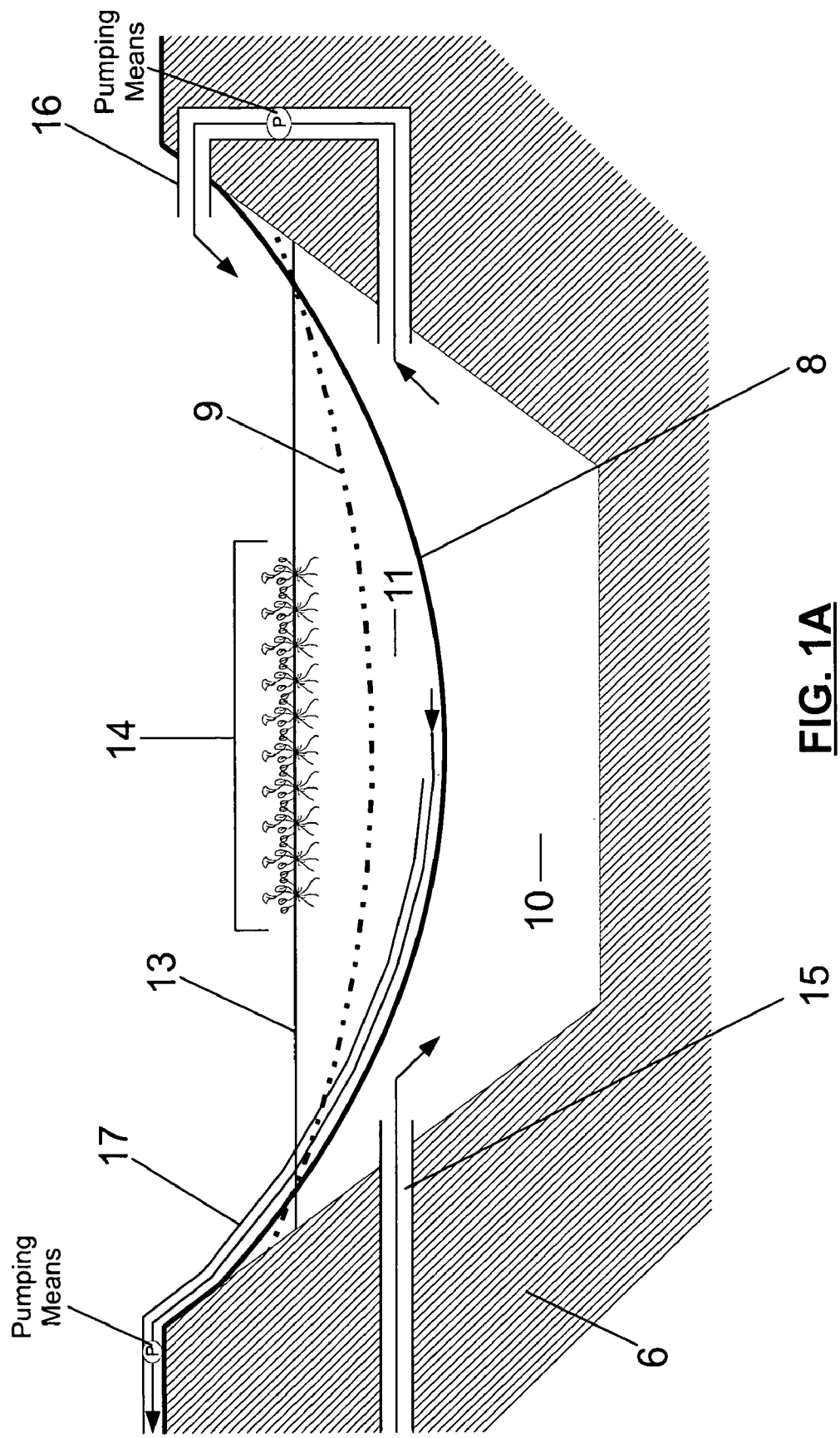

REFERENCE NUMERALS 6 existing or newly constructed anaerobic lagoon
7 floating aquatic plant treatment lagoon
8 sheet of material
9 alternate position of sheet of material
10 anaerobic digestion treatment zone
11 floating aquatic plant treatment zone
12 liquid surface of the anaerobic digestion treatment zone
13 liquid surface of the floating aquatic plant treatment zone
14 floating aquatic plants—water hyacinth (*eichhornia crassipes*)
15 means of conveying untreated wastewater to anaerobic digestion treatment zone
16 means of conveying once treated effluent to floating aquatic plant treatment zone
17 means of conveying twice treated effluent to discharge
18 perforated pipe—biogas preferential pathway
19 non-perforated piping—means for conveying biogas
20 plurality of perforated pipes—biogas preferential pathways
21 untreated wastewater
22 anaerobic digestion treatment
23 conditioning
24 batch floating aquatic plant treatment
25 polishing
26 discharge
26A discharge through granular media filter to the environment
27 first useful purpose
27A combustion of biogas to generate electricity
28 second useful purpose
28A digesting floating aquatic plant biomass in anaerobic digestion treatment zone

DETAILED DESCRIPTION

First Embodiment—FIGS. 1A, 1B, 1C, 1D, 2A

Figure 2A:
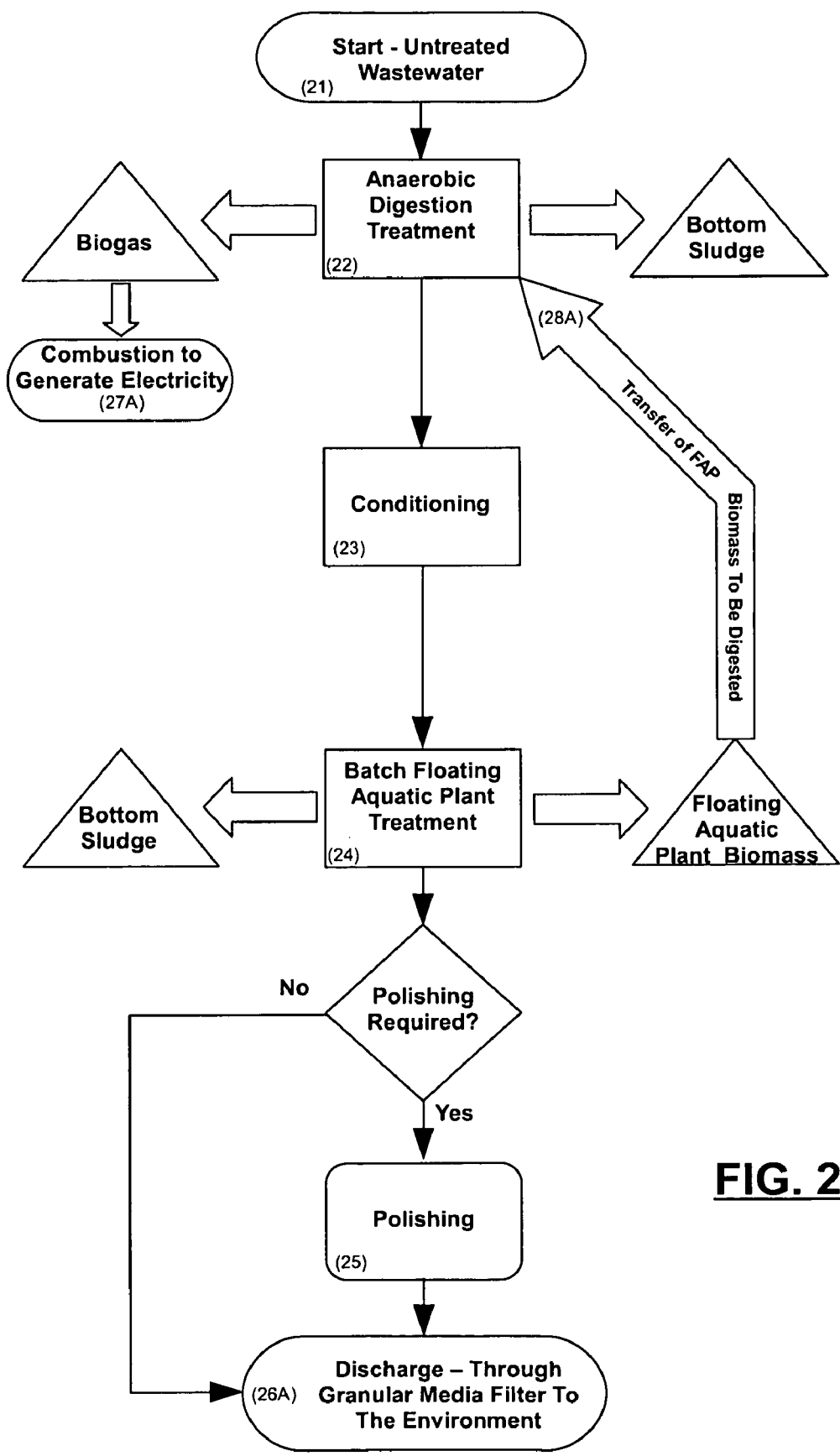
FIG. 2A is a flow chart of an embodiment of the wastewater treatment method that illustrates digesting harvested floating aquatic plant biomass in the anaerobic digestion treatment zone to produce additional biogas and then combusting the biogas to generate electricity.

A first embodiment of the apparatus and method is illustrated by FIGS. 1A-1D and FIG. 2A. FIG. 1A illustrates how a sheet of material 8 subdivides an existing or newly constructed anaerobic lagoon 6 to create an anaerobic digestion treatment zone 10 below the sheet of material 8 and a floating aquatic plant treatment zone 11 above the sheet of material 8. Both treatment zones are sufficiently sized to allow for temporary storage. The sheet of material 8 is flexible and impermeable. The sheet of material's 8 flexibility is illustrated in FIG. 1A with an alternate position of the sheet of material 9 that results from changes in the liquid volume of the two treatment zones. FIG. 1A also illustrates several conveyance means and the direction of flow through the treatment zones. FIGS. 1B-1D illustrate how the sheet of material 8 diverts biogas evolving from anaerobic digestion treatment 22 in the anaerobic digestion treatment zone 10 to a biogas collection means. In this embodiment, the biogas collection means is a plurality perforated pipes 20 that create preferential pathways for biogas to escape from below the sheet of material and non-perforated piping 19 to convey the biogas. FIG. 2A is a flow chart illustrating the method of this embodiment that the apparatus of this embodiment facilitates in an existing or newly constructed anaerobic lagoon 6. In addition, FIG. 2A illustrates the transfer of floating aquatic plant biomass to be digested 28A in the anaerobic digestion treatment zone 10 where additional biogas will be produced and combusted to generate electricity 27A. FIG. 2A also illustrates a conditioning 23 of once treated effluent prior to batch floating aquatic plant treatment 24 and an optional polishing 25 of twice treated effluent prior to discharge 26 and an optional polishing 25 of twice treated effluent prior to discharge through a granular media filter to the environment 26A.

Operation

First Embodiment—FIGS. 1A, 1B, 1C, 1D, 2A

In this first embodiment of the apparatus and method, untreated agricultural animal wastewater 21 is conveyed 15 to an anaerobic digestion treatment zone 10 below a sheet of material 8 where it receives anaerobic digestion treatment 22. Following sufficient anaerobic digestion treatment 22 and temporary storage, the once treated effluent is conveyed 16 to a floating aquatic plant treatment zone 11 above the sheet of material 8 where it undergoes conditioning 23 by diluting it with a retained portion of twice treated effluent from the previous batch. Following dilution, the batch once treated effluent receives floating aquatic plant treatment 24. In this embodiment the floating aquatic plants 14 utilized for treatment are water hyacinth (*eichhornia crassipes*). Following sufficient batch floating aquatic plant treatment 24, the batch of twice treated effluent is optionally polished 25 and then a portion is conveyed 17 to be discharged through a granular media filter to the environment 26A. The remaining portion is for diluting a subsequent batch of once treated effluent. Biogas evolving from anaerobic digestion treatment 22 below the sheet of material 8 is diverted by the sheet of material 8 to a biogas collection means where the biogas is collected and combusted to generate electricity 27A. Floating aquatic plant biomass generated from floating aquatic plant treatment 24 is harvested and transferred to be digested 28A in the anaerobic digestion treatment zone 10. This embodiments use of floating aquatic plant biomass is particularly synergistic as it eliminates the cost of transporting floating aquatic plant biomass and increases the return on the biogas collection means investment by increasing biogas production and generating more electricity.

Batch Floating Aquatic Plant Treatment of Anaerobically Treated Effluent Utilizing Water Hyacinth:

Anaerobic digestion treatment of agricultural animal wastewater is well understood. The following provides information and an example calculation demonstrating how batch floating aquatic plant treatment utilizing water hyacinth (*Eichhornia crassipes*), in conjunction with conventional anaerobic digestion treatment, can substantially treat a years worth of wastewater produced by a swine farm in a single growing season. For locations where the climate allows for year round water hyacinth growth/treatment, treatment goals would only be easier to achieve.

Water Hyacinth Characteristics:
1. Water hyacinth is a floating aquatic plant native to South America and one of the worlds fastest growing plants.
2. The number of water hyacinth plants can more than double in seven days in conditions of high temperature and humidity.
3. One acre of water hyacinth can weigh more than 200 tons (9.2 pounds per square feet); floating mats may double their size in as little as 6-18 days [7].
4. Water hyacinth treats wastewater contaminants by microbial attached growth on the roots, assimilation into biomass, adsorption into biomass, and entrapment in the roots.
    a) Biological oxygen demand (BOD) is treated by microbial attached growth.
    b) N is treated by microbial attached growth.
    c) N and P are treated by assimilation into biomass.
    d) Metals such as copper and iron are treated by assimilation and adsorption into plant biomass.
    e) Suspended solids are treated by entrapment in the root system.
5. Water hyacinth is 92-95% water with a dry weight content of 2.9% N and 0.6% P [5].
6. Water hyacinth has been proven to be able to achieve tertiary standards in continuous flow municipal wastewater treatment systems (BOD<10 mg/l, TN and TP<5 mg/l) [5].
7. Lab experiments have shown that the lower bounds for BOD, N, and P removal using water hyacinth in batch treatments are 1.3 mg/l, 0.2, and 1.4 mg/l respectively [1].
8. Water hyacinth N removal rates have been documented as high as 266 mg per square foot per day [3].
9. In a pilot scale field the present inventor conducted on a swine farm in North Carolina in 2008, water hyacinth exhibited robust growth comparable to the references above in 100% anaerobically treated swine lagoon effluent.

Calculation:

The calculation below demonstrates how the N, P, and BOD contained in anaerobically treated swine farm effluent is substantially treated by batch floating aquatic plant treatment utilizing water hyacinth. While the detailed description of the first embodiment above and referenced figures do not provide dimensions, the liquid surface of the floating aquatic plant treatment zone 13 is assumed to be 50,000 square feet for the purpose of the calculations below.

Parameters for a swine nursery with 2,600 head of swine at 35 pounds/head average [4 and 8]:
1. 91,000 pounds average live weight.
2. 1,200 gallons of wastewater volume accumulation per day.
3. 438,000 gallons of wastewater volume (lagoon effluent) to be treated in batches by floating aquatic plants per year (during the water hyacinth growing season).

Effluent parameters for anaerobic treatment of swine wastewater [2]:
1. BOD=3.33 pounds per 1,000 gallons or 1,459 pounds BOD per year.
2. N=2.91 pounds per 1,000 gallons or 1,275 pounds N year.
3. P=0.63 pounds per 1,000 gallons or 276 pounds P per year.

Based on the parameters listed above, a little less than one million pounds of water hyacinth (wet weight) would have to be grown per growing season to treat all of the wastewater produced by the example swine nursery during a year. One million pounds of wet weight water hyacinth would equal 50,000 pounds of dry weight (using the conservative 5% figure for dry weight). 50,000 pounds of dry weight water hyacinth would equal the removal of 1,450 pounds of N and 300 pounds of P through assimilation alone. This also does not take into consideration the nitrification/de-nitrification route to treat N making the estimate more conservative. BOD is treated by attached growth bacteria grown on the water hyacinth root system and has a removal rate of 0.00067 pounds of BOD per pound of water hyacinth [5]. At this rate, a 100,000 pound mat of water hyacinth would remove 67 pounds of BOD per day. This is the equivalent of treating all 1,459 pounds of BOD used in our example in only 28 days.

One thousand pounds of water hyacinth placed on a 50,000 square foot wastewater surface at the beginning of a growing season would grow to more than 500,000 pounds in 9 weeks. This would equal a 10 pounds per square foot wet weight density. After harvesting to 25% coverage (125,000 pounds) the water hyacinth would grow back to 500,000 pounds in approximately 2 weeks (repeat as necessary). Based on this, 1 million pounds of water hyacinth could be grown in approximately 12 weeks (84 days). For reference, the growing season for water hyacinth would be approximately 120-150 days in North Carolina.

Summary:

Based on the above information and example calculation, it is feasible for batch floating aquatic plant treatment utilizing water hyacinth (*eichhornia crassipes*), in conjunction with conventional anaerobic digestion treatment, to substantially treat a years worth of wastewater produced by the example swine nursery in a single growing season.

Advantages:

Thus, the reader will see that the first embodiment of the method and apparatus provides a technically, operationally, and economically feasible agricultural animal wastewater treatment system that costs less to build, is easier to understand and operate, and requires little energy input. In addition to eliminating the discharge of animal waste to surface waters and groundwater, this embodiment also:

1. Substantially eliminates atmospheric emissions of ammonia,
    The apparatus' sheet of material acts as a cover over the anaerobic digestion treatment zone which significantly reduces ammonia volatilization to the atmosphere. In addition, retaining a portion of twice treated effluent in the floating aquatic plant zone for the purpose of diluting a subsequent batch of once treated effluent lowers both the ammonia concentration and its pH. Lower concentrations of ammonia and pH also significantly reduce ammonia volatilization to the atmosphere.
2. Substantially eliminates the emission of odor,
    The apparatus' sheet of material acting as a cover over the anaerobic digestion treatment zone as well as the collection and combustion of biogas evolving from anaerobic digestion treatment significantly reduces odor emissions.
3. Substantially eliminates the release of disease-transmitting vectors and airborne pathogens, and
    The apparatus' sheet of material acting as a cover over the anaerobic digestion treatment zone eliminates the release of disease-transmitting vectors and airborne pathogens. Conventional anaerobic treatment lagoon hydraulic retention times are around 180 days which is more than sufficient to significantly reduce pathogens. Natural systems such as those employed by the apparatus and method provide very effective control of disease transmitting vectors and airborne pathogens. Large floating mats of water hyacinth provide habitat for animals species such as frogs that help control mosquito populations.
4. Substantially eliminates nutrient and heavy metal contamination of soil and groundwater.
    Nutrients are removed through anaerobic digestion and batch floating aquatic plant treatment. P is removed by water hyacinth through assimilation. N is removed through assimilation and attached microbial growth on the root system. Metals such as iron and copper treated by water hyacinth through assimilation and adsorption into plant biomass.

Description

Second Embodiment—FIGS. 1A, 1B, 1C, 1D, 2B

Figure 2B:
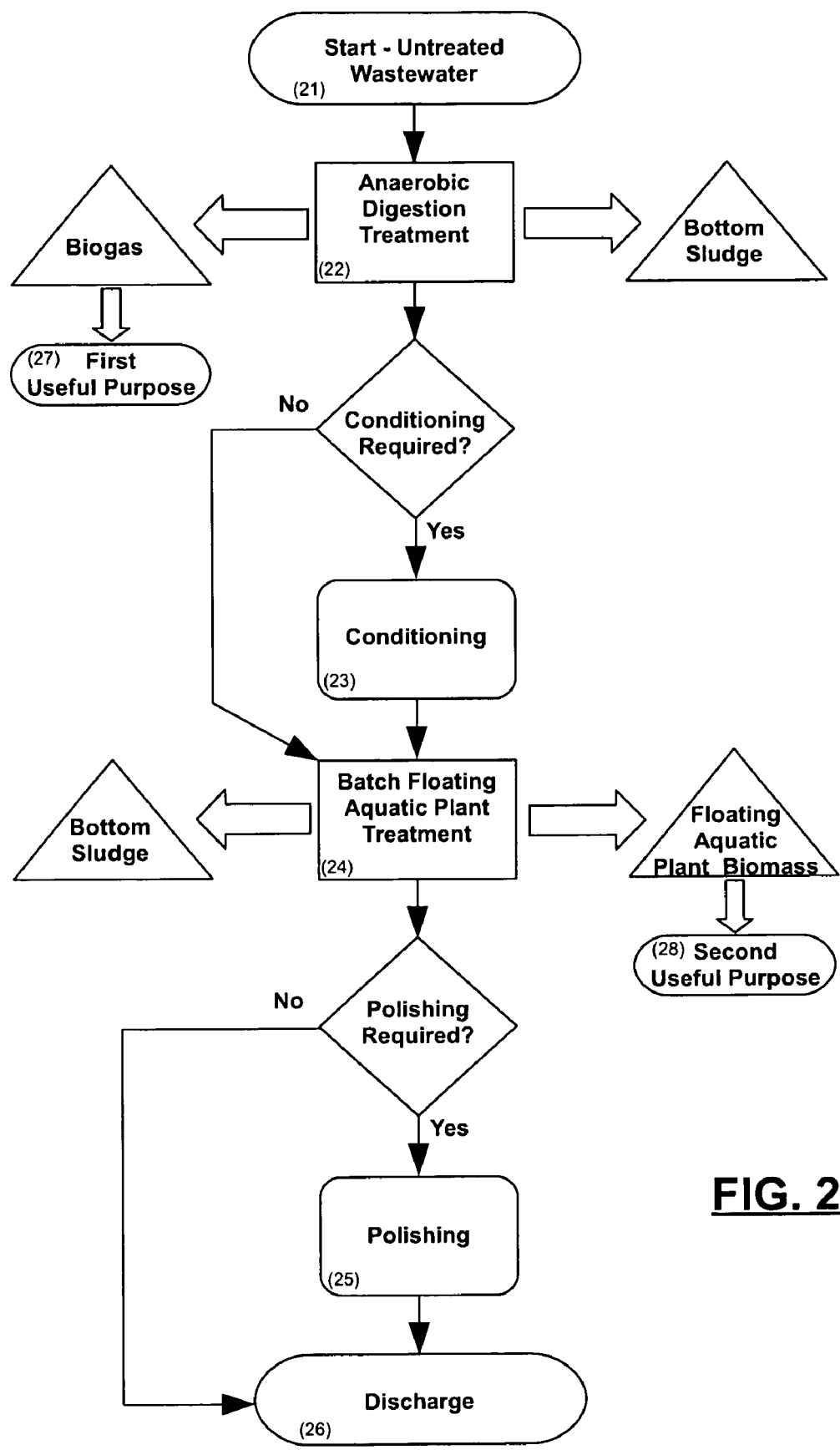
FIG. 2B is a flow chart of an embodiment of the wastewater treatment method that illustrates generic useful purposes for biogas or floating aquatic plant biomass.

A second embodiment of the apparatus and method is illustrated by FIGS. 1A-1D and FIG. 2B and is very similar to the first embodiment with the exception being the absence of specificities related to the useful purposes for biogas and floating aquatic plant biomass. FIG. 1A illustrates how a sheet of material 8 subdivides an existing or newly constructed anaerobic lagoon 6 to create an anaerobic digestion treatment zone 10 below the sheet of material 8 and a floating aquatic plant treatment zone 11 above the sheet of material 8. Both treatment zones are sufficiently sized to allow for temporary storage. The sheet of material 8 is flexible and impermeable. The sheet of material's 8 flexibility is illustrated in FIG. 1A with an alternate position of the sheet of material 9 that results from changes in the liquid volume of the two treatment zones. FIGS. 1B-1D illustrate how the sheet of material 8 diverts biogas evolving from anaerobic digestion 22 in the anaerobic digestion treatment zone 10 to a biogas collection means. In this embodiment, the biogas collection means is a plurality perforated pipes 20 that create preferential pathways for biogas to escape from below the sheet of material and non-perforated piping 19 to convey the biogas to be utilized for a first useful purpose 27. FIG. 2B is a flow chart illustrating the method of this embodiment that the apparatus of this embodiment facilitates in an existing or newly constructed anaerobic lagoon 6. In addition, FIG. 2B illustrates the opportunistic collection and use of byproducts from anaerobic digestion treatment 22 (biogas) and batch floating aquatic plant treatment 24 (biomass), as well as an optional conditioning 23 of once treated effluent prior to batch floating aquatic plant treatment 24 and an optional polishing 25 of twice treated effluent prior to discharge 26.

Operation

Second Embodiment—FIGS. 1A, 1B, 1C, 1D, 2B

In this second embodiment of the apparatus and method, untreated agricultural animal wastewater 21 is conveyed 15 to an anaerobic digestion treatment zone 10 below a sheet of material 8 where it receives anaerobic digestion treatment 22. Following sufficient anaerobic digestion treatment 22 and temporary storage, the once treated effluent is conveyed 16 to a floating aquatic plant treatment zone 11 above the sheet of material 8 where it is optionally conditioned 23 prior to receiving batch floating aquatic plant treatment 24. In this embodiment the floating aquatic plants 14 utilized for treatment are water hyacinth (*eichhornia crassipes*). Following sufficient batch floating aquatic plant treatment 24, the batch of twice treated effluent is optionally polished 25 and then conveyed 17 to be discharged 26. Biogas evolving from anaerobic digestion treatment 22 below the sheet of material 8 is diverted by the sheet of material 8 to a biogas collection means where the biogas is collected to be used for a first useful purpose 27. Floating aquatic plant biomass generated from floating aquatic plant treatment 24 is harvested from the floating aquatic plant treatment zone 11 to be used for a second useful purpose 28.

Description

Figure 2C:
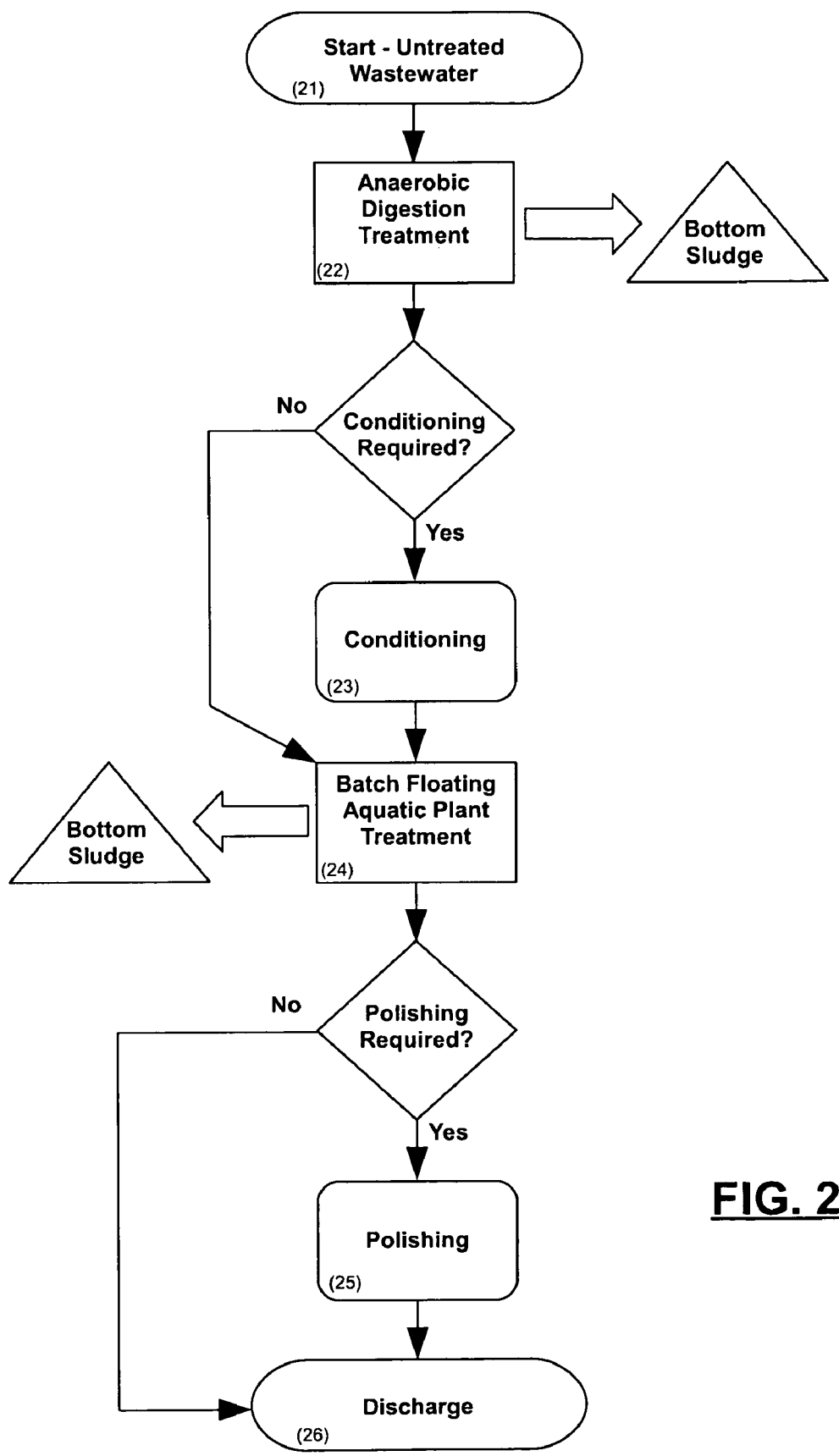
FIG. 2C is a flow chart illustrating an embodiment of the wastewater treatment method that does not incorporate useful purposes for biogas or floating aquatic plant biomass.

Third Embodiment—FIGS. 1A and 2C

A third embodiment of the apparatus and method is illustrated by FIGS. 1A and 2C and is very similar to the second embodiment with the exception being that this embodiment does not incorporate a biogas collection means or useful purposes for biogas or floating aquatic plant biomass. FIG. 1A illustrates how a sheet of material 8 subdivides an existing or newly constructed anaerobic lagoon 6 to create an anaerobic digestion treatment zone 10 below the sheet of material 8 and a floating aquatic plant treatment zone 11 above the sheet of material 8. Both treatment zones are sufficiently sized to allow for temporary storage. The sheet of material 8 is flexible and impermeable. The sheet of material's 8 flexibility is illustrated in FIG. 1A with an alternate position of the sheet of material 9 that results from changes in the liquid volume of the two treatment zones. FIG. 2C is a flow chart illustrating the method of this embodiment that the apparatus of this embodiment facilitates in an existing or newly constructed anaerobic lagoon 6. In addition, FIG. 2C illustrates an optional conditioning 23 of once treated effluent prior to batch floating aquatic plant treatment 24 and an optional polishing 25 of twice treated effluent prior to discharge 26.

Operation

Third Embodiment—FIGS. 1A and 2C

In this third embodiment of the apparatus and method, untreated agricultural animal wastewater 21 is conveyed 15 to an anaerobic digestion treatment zone 10 below a sheet of material 8 where it receives anaerobic digestion treatment 22. Following sufficient anaerobic digestion treatment 22 and temporary storage, the once treated effluent is conveyed 16 to a floating aquatic plant treatment zone 11 above the sheet of material 8 where it is optionally conditioned 23 prior to receiving batch floating aquatic plant treatment 24. In this embodiment the floating aquatic plants 14 utilized for treatment are water hyacinth (*eichhornia crassipes*). Following sufficient batch floating aquatic plant treatment 24, the batch of twice treated effluent is optionally polished 25 and then conveyed 17 to be discharged 26.

Description

Figure 2D:
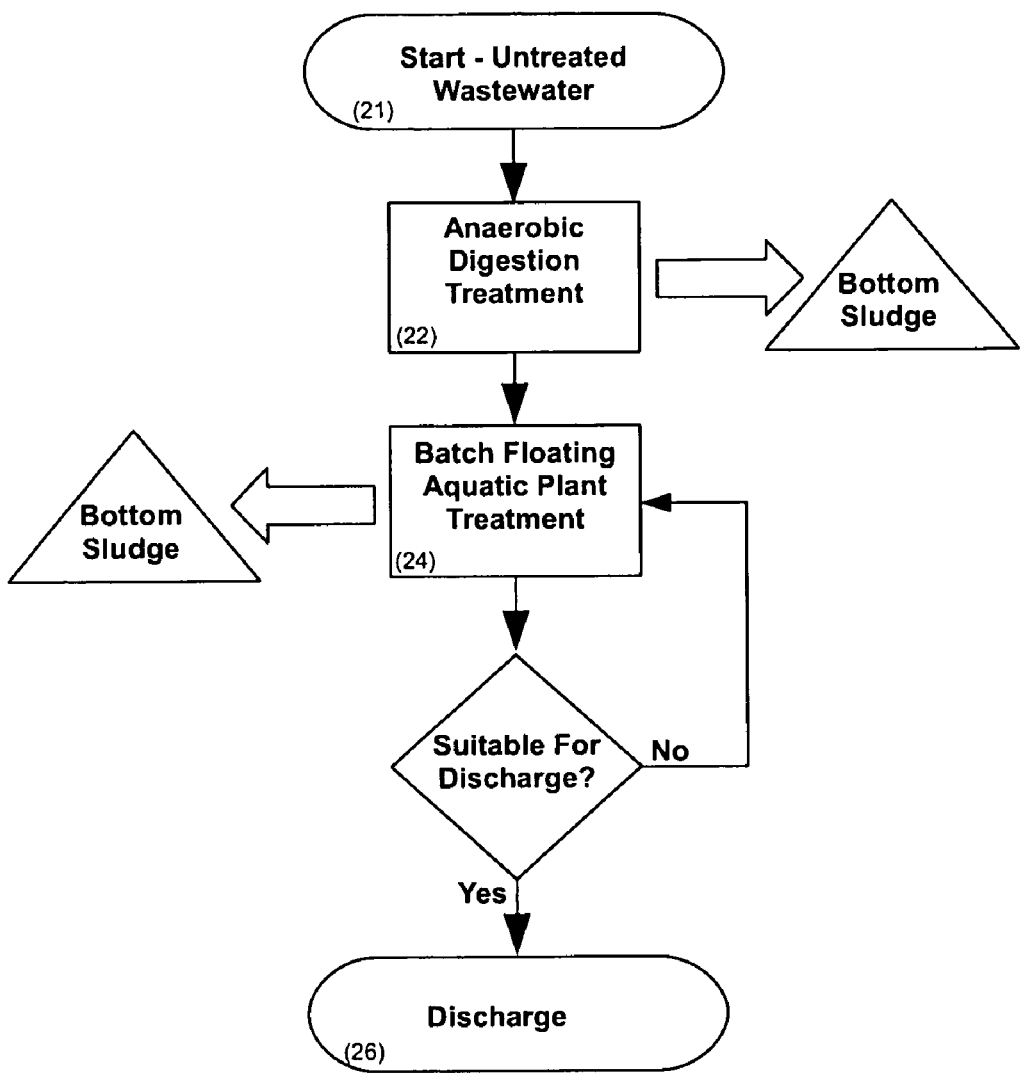
FIG. 2D is a flow chart illustrating a basic embodiment of the wastewater treatment method that does not incorporate useful purposes for biogas or floating aquatic plant biomass. It also does not incorporate conditioning of once treated effluent or polishing of twice treated effluent.

Fourth Embodiment—FIGS. 1A and 2D

A fourth embodiment of the apparatus and method is illustrated by FIGS. 1A and 2D and is very similar to the third embodiment with a couple of exceptions. This embodiment does not incorporate a biogas collection means or useful purposes for biogas or floating aquatic plant biomass, nor does it incorporate conditioning 23 of once treated effluent prior to batch floating aquatic plant treatment 24 or polishing 25 of twice treated effluent prior to discharge 26. FIG. 1A illustrates how a sheet of material 8 subdivides an existing or newly constructed anaerobic lagoon 6 to create an anaerobic digestion treatment zone 10 below the sheet of material 8 and a floating aquatic plant treatment zone 11 above the sheet of material 8. Both treatment zones are sufficiently sized to allow for temporary storage. The sheet of material 8 is flexible and impermeable. The sheet of material's 8 flexibility is illustrated in FIG. 1A with an alternate position of the sheet of material 9 that results from changes in the liquid volume of the two treatment zones. FIG. 2D is a flow chart illustrating the method of this embodiment that the apparatus of this embodiment facilitates in an existing or newly constructed anaerobic lagoon 6.

Operation

Fourth Embodiment—FIGS. 1A and 2D

In this fourth embodiment of the apparatus and method, untreated agricultural animal wastewater 21 is conveyed 15 to an anaerobic digestion treatment zone 10 below a sheet of material 8 where it receives anaerobic digestion treatment 22. Following sufficient anaerobic digestion treatment 22 and temporary storage, the once treated effluent is conveyed 16 to a floating aquatic plant treatment zone 11 above the sheet of material 8 where it receives batch floating aquatic plant treatment 24. In this embodiment the floating aquatic plants 14 utilized for treatment are water hyacinth (*Eichhornia crassipes*). Following sufficient batch floating aquatic plant treatment 24, the batch of twice treated effluent is then conveyed 17 to be discharged 26.

Description

Additional Embodiments—FIGS. 2A, 2B, 2C, 2D

Additional embodiments are illustrated as flow charts in FIGS. 2A-2D. Each of these flow charts represent individual embodiments of the method independent of the apparatus.

FIG. 2A illustrates the opportunistic collection and use of byproducts from anaerobic digestion treatment 22 (biogas) and batch floating aquatic plant treatment 24 (biomass), as well as a conditioning 23 of once treated effluent prior to batch floating aquatic plant treatment 24 and an optional polishing 25 of twice treated effluent prior to discharge through a granular media filter to the environment 26A. In addition, FIG. 2A illustrates the transfer of floating aquatic plant biomass to be digested 28A in the anaerobic digestion treatment zone 10 where additional biogas will be produced and combusted to generate electricity 27A.

FIG. 2B illustrates the opportunistic collection and use of byproducts from anaerobic digestion treatment 22 (biogas) and batch floating aquatic plant treatment 24 (biomass), as well as an optional conditioning 23 of once treated effluent prior to floating aquatic plant treatment and an optional polishing 25 of twice treated effluent prior to discharge 26.

FIG. 2C illustrates an optional conditioning 23 of once treated effluent prior to floating aquatic plant treatment and an optional polishing 25 of twice treated effluent prior to discharge 26.

FIG. 2D is a flow chart illustrating a basic embodiment of the method.

Operation

Additional Embodiments—FIGS. 2A, 2B, 2C, 2D

In the FIG. 2A embodiment of the method, untreated agricultural animal wastewater 21 is conveyed 15 to an anaerobic digestion treatment zone 10 where it receives anaerobic digestion treatment 22. Following sufficient anaerobic digestion treatment 22 and temporary storage, the once treated effluent is conveyed 16 to a floating aquatic plant treatment zone 11 where it undergoes conditioning 23 by diluting it with a retained portion of twice treated effluent from the previous batch. Following dilution, the batch once treated effluent receives floating aquatic plant treatment 24. In this embodiment the floating aquatic plants 14 utilized for treatment are water hyacinth (*Eichhornia crassipes*). Following sufficient batch floating aquatic plant treatment 24, the batch of twice treated effluent is optionally polished 25 and then a portion is conveyed 17 to be discharged through a granular media filter to the environment 26A. The remaining portion is for diluting a subsequent batch of once treated effluent. Biogas evolving from anaerobic digestion treatment 22 below the sheet of material 8 is diverted by the sheet of material 8 to a biogas collection means where the biogas is collected and combusted to generate electricity 27A. Floating aquatic plant biomass generated from floating aquatic plant treatment 24 is harvested and transferred to be digested 28A in the anaerobic digestion treatment zone 10. This embodiments use of floating aquatic plant biomass is particularly synergistic as it eliminates the cost of transporting floating aquatic plant biomass and increases the return on the biogas collection means investment by increasing biogas production and generating more electricity.

In the FIG. 2B embodiment of the method, untreated agricultural animal wastewater 21 is conveyed 15 to an anaerobic digestion treatment zone 10 where it receives anaerobic digestion treatment 22. Following sufficient anaerobic digestion treatment 22 and temporary storage, the once treated effluent is conveyed 16 in to a floating aquatic plant treatment zone 11 where it is optionally conditioned 23 prior to receiving batch floating aquatic plant treatment 24. In this embodiment the floating aquatic plants 14 utilized for treatment are water hyacinth (*Eichhornia crassipes*). Following sufficient batch floating aquatic plant treatment 24, the batch of twice treated effluent is optionally polished 25 and then conveyed 17 to be discharged 26. Biogas evolving from anaerobic digestion treatment 22 is collected by a biogas collection means to be used for a first useful purpose 27. Floating aquatic plant biomass generated from floating aquatic plant treatment 24 is harvested from the floating aquatic plant treatment zone 11 to be used for a second useful purpose 28.

In the FIG. 2C embodiment of the method, untreated agricultural animal wastewater 21 is conveyed 15 to an anaerobic digestion treatment zone 10 where it receives anaerobic digestion treatment 22. Following sufficient anaerobic digestion treatment 22 and temporary storage, the once treated effluent is conveyed 16 to a floating aquatic plant treatment zone 11 where it is optionally conditioned 23 prior to receiving batch floating aquatic plant treatment 24. In this embodiment the floating aquatic plants 14 utilized for treatment are water hyacinth (*Eichhornia crassipes*). Following sufficient batch floating aquatic plant treatment 24, the batch of twice treated effluent is optionally polished 25 and then conveyed 17 to be discharged 26.

In the FIG. 2D embodiment of the method, untreated agricultural animal wastewater 21 is conveyed 15 to an anaerobic digestion treatment zone 10 where it receives anaerobic digestion treatment 22. Following sufficient anaerobic digestion treatment 22 and temporary storage, the once treated effluent is conveyed 16 to a floating aquatic plant treatment zone 11 where it receives batch floating aquatic plant treatment 24. In this embodiment the floating aquatic plants 14 utilized for treatment are water hyacinth (*Eichhornia crassipes*). Following sufficient batch floating aquatic plant treatment 24, the batch of twice treated effluent is then conveyed 17 to be discharged 26.

Description

Alternative Embodiments—FIGS. 3, 2A, 2B, 2C, 2D

There are various possibilities for how the method could be implemented independent of the apparatus. The alternative embodiment illustrated in FIG. 3 utilizes two lagoons; an existing or newly constructed anaerobic lagoon 6 for anaerobic digestion treatment 22 and a floating aquatic plant treatment lagoon 7 for batch floating aquatic plant treatment 24. Both lagoons are sufficiently sized to allow for temporary storage. In this embodiment the floating aquatic plants 14 utilized for treatment are water hyacinth (*eichhornia crassipes*). This configuration could facilitate the methods illustrated by FIG. 2C or FIG. 2D.

Another alternative embodiment (no Fig.) would be the two lagoon set up illustrated in FIG. 3 and described above including a biogas capture means over the existing or newly constructed anaerobic lagoon 6. This configuration could facilitate the methods illustrated by FIG. 2A or FIG. 2B.

CONCLUSION, RAMIFICATIONS, AND SCOPE

Accordingly, the reader will see that one or more embodiments of the method and apparatus provide a technically, operationally, and economically feasible agricultural animal wastewater treatment system that costs less to build, is easier to understand and operate, and requires little energy input. In addition one ore more embodiments 1. Eliminates the discharge of animal waste to surface waters and groundwater,
2. Substantially eliminates atmospheric emissions of ammonia,
3. Substantially eliminates the emission of odor,
4. Substantially eliminates the release of disease-transmitting vectors and airborne pathogens, and
5. Substantially eliminates nutrient and heavy metal contamination of soil and groundwater.

While the above descriptions contain many specificities, these should not be construed as limitations on the scope of any embodiment, but as exemplifications of the presently preferred embodiments thereof. Many other ramifications and variations are possible within the teachings of the various embodiments. For example, various other types (species) or combinations of floating aquatic plant types can be utilized for floating aquatic plant treatment; the size, shape, or composition of the sheet of material can vary; the liquid conveyance means' can have many different forms; the biogas conveyance and collection means can have many different forms; the type, size, volume, liquid surface area, and number of reservoirs making up the two treatment zones could vary, etc. Thus, the scope of the invention should be determined by the appended claims and their legal equivalents, and not by the examples given.

REFERENCES

1) Advanced Extraction and Lower Bounds for Removal of Pollutants from Wastewater by Water Plants, Water Environment Research, March 2007, Vol 79, Issue 3, p 287-296, Zimmels et al.

2) Agricultural Waste Management Field Handbook (210-AWMFH, 4/92) 1-19, United States Department of Agriculture (USDA).
3) Feasibility Manual for Aquatic Plant Wastewater Treatment with Energy Recovery, Chynoweth 1989.
4) Manure Production Nutrient Content Data, (USDA) Natural Resource Conservation Service.
5) Natural Systems for Waste Management and Treatment, Reed, 1988.
6) North Carolina State University College of Agriculture and Life Sciences' Smithfield Agreement website: http://www.cals.ncsu.edu/waste_mgt/smithfield_projects/smithfieldsite.htm
7) The Growth and Management of *Eichhornia Crassipes* and *Salvinia* spp. in Their Native Environment and in Alien Situations, Mitchell D S. 1976.
8) U.S. Manure Management Inventory, Environmental Protection Agency, 2004.

I claim:

1. A method for treating wastewater, comprising:
   (a) conveying said wastewater to a first zone, said first zone being of predetermined size and conducive to anaerobic digestion treatment,
   (b) providing said first zone where:
      (1) said wastewater is treated via anaerobic digestion,
      (2) a once treated effluent is produced following anaerobic digestion, and
      (3) bottom sludge is periodically removed,
   (c) conveying said once treated effluent from said first zone to a second zone, said second zone being:
      (1) of predetermined size,
      (2) exposed to sunlight and the atmosphere, and
      (3) conducive to floating aquatic plant treatment,
   (d) conditioning said once treated effluent prior to floating aquatic plant treatment,
   (e) providing said second zone where:
      (1) batches of said once treated effluent receive floating aquatic plant treatment by growing a multitude of at least one type of floating aquatic plant on the surface of said once treated effluent,
      (2) batches of a twice treated effluent are produced following floating aquatic plant treatment,
      (3) floating aquatic plant biomass from floating aquatic plant growth is periodically harvested, and
      (4) bottom sludge is periodically removed,
   (f) discharging batches of said twice treated effluent from said second zone,
   whereby said wastewater is treated by anaerobic digestion in said first zone and conditioning of said once treated effluent facilitates floating aquatic plant treatment in said second zone.

2. The method of claim 1 wherein said wastewater is one of:
   (a) biodegradable agricultural animal wastewater,
   (b) biodegradable wastewater,
   (c) biodegradable municipal wastewater,
   (d) biodegradable domestic wastewater, and
   (e) biodegradable industrial wastewater.

3. The method of claim 1 wherein the type of floating aquatic plant includes at least one of
   (a) water hyacinths,
   (b) duckweeds,
   (c) pennywort, and
   (d) water ferns.

4. The method of claim 1 wherein floating aquatic plant treatment comprises at least one of:
   (a) assimilating macronutrients, micronutrients, and metals into floating aquatic plant biomass,
   (b) attached microbial growth on the roots of floating aquatic plants,
   (c) adsorption of metals and suspended solids by floating aquatic plants, and
   (d) entrapment of suspended solids in the root zone of the floating aquatic plants.

5. The method of claim 1 wherein floating aquatic plant treatment takes place during the growing season of the type of floating aquatic plants being utilized.

6. The method of claim 1 further comprising collecting biogas evolving from anaerobic digestion in said first zone to be used for a first useful purpose.

7. The method of claim 6 wherein said first useful purpose includes at least one of:
   (a) use as a source of energy via combustion of said biogas,
   (b) use as a source of heat via combustion of said biogas, and
   (c) use as a source of electricity via combustion of said biogas.

8. The method of claim 1 further comprising utilizing said floating aquatic plant biomass harvested from said second zone for a second useful purpose.

9. The method of claim 8 wherein said second useful purpose includes at least one of:
   (a) use as a source of biogas via anaerobic digestion of said floating aquatic plant biomass in said first zone,
   (b) use as a source of biogas via anaerobic digestion of said floating aquatic plant biomass,
   (c) use as an animal feed,
   (d) use as compost,
   (e) use as a green manure,
   (f) use as a fertilizer, and
   (g) use as an energy source via incineration of said floating aquatic plant biomass.

10. The method of claim 1 wherein said conditioning includes at least one of:
    (a) adding chemicals to adjust the pH,
    (b) adding chemicals to adjust the alkalinity,
    (c) adding chemicals to control algal growth,
    (d) adding chemicals to control disease-transmitting vectors,
    (e) adding chemicals to control insects,
    (f) adding water for the purpose of dilution,
    (g) adding water to reduce the salinity,
    (h) adding macronutrients, and
    (i) adding micronutrients.

11. The method of claim 1 further comprising polishing said twice treated effluent prior to discharging.

12. The method of claim 11 wherein said polishing includes at least one of:
    (a) volatilizing ammonium nitrogen,
    (b) adding chemicals to adjust the pH,
    (c) precipitating suspended solids via chemical precipitation, and
    (d) precipitating phosphorus via chemical precipitation.

13. The method of claim 1 further comprising temporarily storing said once treated effluent in at least one of said first zone and said second zone prior to receiving floating aquatic plant treatment.

14. The method of claim 1 further including retaining a portion of twice treated effluent in said second zone for the purpose of diluting a subsequent batch of once treated effluent.

15. The method of claim 1 wherein discharging of said twice treated effluent from said second zone is to at least one of:
    (a) a reuse means, (b) a granular media filter,
(c) an animal confinement facility,
(d) spray fields,
(e) a wetland, and
(f) the environment.

16. An apparatus for treatment of wastewater in a reservoir, comprising:
   (a) a sheet of material, said sheet of material being flexible, impermeable, of predetermined size, and disposed in said reservoir such that:
      (1) a first zone conducive to anaerobic digestion treatment is created below said sheet of material where:
         (A) said wastewater is treated via anaerobic digestion,
         (B) a once treated effluent is produced following anaerobic digestion, and
         (C) bottom sludge is periodically removed,
      (2) a second zone exposed to the sun and atmosphere and conducive to floating aquatic plant treatment is created above said sheet of material where:
         (A) batches of said once treated effluent receives floating aquatic plant treatment by growing a multitude of at least one type of floating aquatic plant on the surface of said once treated effluent,
         (B) batches of a twice treated effluent are produced following floating aquatic plant treatment,
         (C) floating aquatic plant biomass from floating aquatic plant growth is periodically harvested, and
         (D) bottom sludge is periodically removed,
      (3) sufficient slack is provided in said sheet of material to compensate for changes in the liquid volume of at least one of said first zone and said second zone,
   (b) a first means for conveying said wastewater to said first zone,
   (c) a second means for conveying said once treated effluent from said first zone to said second zone, and
   (d) a third means for discharging batches of said twice treated effluent from said second zone,
   whereby said sheet of material is disposed in said reservoir such that said first zone conducive to anaerobic digestion treatment and said second zone conducive to floating aquatic plant treatment are created, and sufficient slack is provided in said sheet of material to compensate for changes in the liquid volume of at least one of said first zone and said second zone.

17. The apparatus of claim 16 wherein said reservoir is one of:
   (a) an existing anaerobic lagoon,
   (b) a lagoon,
   (c) a pond,
   (d) a tank, and
   (e) a concrete cell.

18. The apparatus of claim 16 wherein said sheet of material is composed of at least one of:
   (a) high density polyethylene,
   (b) medium density polyethylene,
   (c) polyethylene,
   (d) polyvinyl chloride,
   (e) polypropylene,
   (f) ethylene propylene diene M-class rubber, and
   (g) rubber.

19. The apparatus of claim 16 wherein said sheet of material is disposed in said reservoir such that biogas evolving from anaerobic digestion in said first zone is diverted by said sheet of material to at least one area to be collected and used for a first useful purpose.

20. The apparatus of claim 19 wherein said first useful purpose includes at least one of:

(a) use as a source of energy via combustion of said biogas,
   (b) use as a source of heat via combustion of said biogas, and
   (c) use as a source of electricity via combustion of said biogas.

21. The apparatus of claim 16 wherein said floating aquatic plant biomass from floating aquatic plant growth in said second zone is periodically harvested to be used for a second useful purpose.

22. The apparatus of claim 21 wherein said second useful purpose includes at least one of:
   (a) use as a source of biogas via anaerobic digestion of said floating aquatic plant biomass in said first zone,
   (b) use as a source of biogas via anaerobic digestion of said floating aquatic plant biomass,
   (c) use as an animal feed,
   (d) use as compost,
   (e) use as a green manure,
   (f) use as a fertilizer, and
   (g) use as an energy source via incineration of said floating aquatic plant biomass.

23. The apparatus of claim 16 wherein at least one of said first zone and said second zone are sufficiently sized to allow for temporary storage of said once treated effluent prior to it receiving floating aquatic plant treatment.

24. An apparatus for treatment of wastewater in a reservoir, comprising:
   (a) a sheet of material, said sheet of material being flexible, impermeable, of predetermined size, and disposed in said reservoir such that:
      (1) a first zone conducive to anaerobic digestion treatment is created below said sheet of material where:
         (A) said wastewater is treated via anaerobic digestion,
         (B) a once treated effluent is produced following anaerobic digestion, and
         (C) bottom sludge is periodically removed,
      (2) a second zone exposed to the sun and atmosphere and conducive to floating aquatic plant treatment is created above said sheet of material where:
         (A) batches of said once treated effluent receives floating aquatic plant treatment by growing a multitude of at least one type of floating aquatic plant on the surface of said once treated effluent,
         (B) batches of a twice treated effluent are produced following floating aquatic plant treatment,
         (C) floating aquatic plant biomass from floating aquatic plant growth is periodically harvested and used for a second useful purpose, and
         (D) bottom sludge is periodically removed,
      (3) sufficient slack is provided in said sheet of material to compensate for changes in the liquid volume of at least one of said first zone and said second zone, and
      (4) biogas evolving from anaerobic digestion in said first zone is diverted by said sheet of material to at least one area to be collected and used for a first useful purpose,
   (b) a first means for conveying said wastewater to said first zone,
   (c) a second means for conveying said once treated effluent from said first zone to said second zone,
   (d) a third means for collecting said biogas diverted by said sheet of material, and
   (e) a fourth means for discharging batches of said twice treated effluent from said second zone,
   whereby said sheet of material is disposed in said reservoir such that said first zone conducive to anaerobic digestion treatment and said second zone conducive to floating aquatic plant treatment are created, sufficient slack is provided in said sheet of material to compensate for changes in the liquid volume of at least one of said first zone and said second zone, and biogas is diverted to at least one area to be collected and used for said first useful purpose.

25. The apparatus of claim 24 wherein said reservoir is one of:
   (a) an existing anaerobic lagoon,
   (b) a lagoon,
   (c) a pond,
   (d) a tank, and
   (e) a concrete cell.

26. The apparatus of claim 24 wherein said sheet of material is composed of at least one of:
   (a) high density polyethylene,
   (b) medium density polyethylene,
   (c) polyethylene,
   (d) polyvinyl chloride,
   (e) polypropylene,
   (f) ethylene propylene diene M-class rubber, and
   (g) rubber.

27. The apparatus of claim 24 wherein said first useful purpose includes at least one of:
   (a) use as a source of energy via combustion of said biogas,
   (b) use as a source of heat via combustion of said biogas, and
   (c) use as a source of electricity via combustion of said biogas.

28. The apparatus of claim 24 wherein said second useful purpose includes at least one of:
   (a) use as a source of biogas via anaerobic digestion of said floating aquatic plant biomass in said first zone,
   (b) use as a source of biogas via anaerobic digestion of said floating aquatic plant biomass,
   (c) use as an animal feed,
   (d) use as compost,
   (e) use as a green manure,
   (f) use as a fertilizer, and
   (g) use as an energy source via incineration of said floating aquatic plant biomass.

29. The apparatus of claim 24 wherein at least one of said first zone and said second zone are sufficiently sized to allow for temporary storage of said once treated effluent prior to it receiving floating aquatic plant treatment.

* * * * *